United States Patent [19]

Whitten et al.

[11] Patent Number: 4,508,105
[45] Date of Patent: Apr. 2, 1985

[54] SHADOW GENERATING APPARATUS

[76] Inventors: Glen A. Whitten; Lech Pisarski, both of 353 N. Oak St., Inglewood, Calif. 90302

[21] Appl. No.: 464,970

[22] Filed: Feb. 8, 1983

[51] Int. Cl.³ .............................................. A61M 21/00
[52] U.S. Cl. ..................................................... 128/1 C
[58] Field of Search ....................................... 128/1 C

[56] References Cited

U.S. PATENT DOCUMENTS

| | | | |
|---|---|---|---|
| 569,117 | 10/1896 | Mosher | 128/1 C |
| 3,722,501 | 3/1973 | Derouineau | 128/1 C |
| 3,972,319 | 8/1976 | Dehlinger | 128/1 C |
| 4,315,502 | 2/1982 | Gorges | 128/1 C |

FOREIGN PATENT DOCUMENTS 16357 of 1899 United Kingdom ............... 128/1 C

Primary Examiner—William E. Kamm
Attorney, Agent, or Firm—Oldham, Oldham & Weber Co.

[57] ABSTRACT

Disclosed is an apparatus for inducing various brain wave patterns through visual stimulation. The apparatus comprises a pair of spectacles or other viewing apparatus having a liquid crystal display embedded in each lens. By repetitively activating and deactivating the liquid crystals, shadows are generated which are perceived by the subject individual wearing the viewing apparatus. Responding to the frequency of shadow generation, the subject's brain is thereby induced to generate sympathetic brain wave frequencies. The apparatus finds particular utility in the generation of alpha waves. Because learning is enhanced when the brain is in the alpha state, activities such as listening to tapes or lectures and the like can be carried out with greater facility. Shadow generation is accomplished through the use of a timing mechanism for each liquid crystal display and the frequency for each is adjustable over a wide range, permitting synchronous or asynchronous timing.

8 Claims, 5 Drawing Figures

SHADOW GENERATING APPARATUS

TECHNICAL FIELD

The present invention lies in the art of relaxation inducing devices, and in particular it relates to the field of visual stimulation through repetitive generation of shadows. By variation of the frequency in which said shadows are generated, the desired state of mind is attained, characterized by a specific wave pattern.

BACKGROUND ART

Heretofore, a multitude of devices have been used for controlling the brain wave activity of a human subject. Certain of the prior art inventions produce the required effect through electrical or chemical stimulation of the nervous system. Others make use of flashing lights or sounds. While all such devices may be effective to a greater or lesser degree, they have certain drawbacks. For example, direct chemical or electrical nerve stimulation can have serious side effects such as temporary loss of memory, lethargy and the like. Flashing lights or sounds have been known to produce epileptic seizures in susceptible individuals and are at the very least distracting.

The alpha state characterized by a particular brain wave pattern, is manifested by a high degree of alertness found to be conducive to learning.

By way of prior art devices are the following U.S. Pat. Nos.: 3,219,028 to Giordino; 3,255,753 to Wing; 3,470,870 to Schoffer; 3,384,074 to Nautiola, et al; 3,712,292 to Zentmeyer; 3,718,132 to Holt, et al; 3,722,501 to Derouineau; 3,762,396 to Valentine, et al; 3,822,693 to King; 3,884,218 to Monroe; 3,967,616 to Ross; 3,993,043 to Adams, et al; 4,018,218 to Carlson, et al; 4,047,377 to Banks; 4,133,305 to Steuer; 4,157,088 to Gracey; 4,227,516 to Meland, et al; 4,282,864 to Pizer; 4,335,710 to Williamson; and 3,773,049 to Rabichev, et al.

DISCLOSURE OF THE INVENTION

It is accordingly an aspect of the invention to provide a device which induces a desired brain wave pattern through the generation of shadows.

Another aspect of the invention is to provide a device, as above, which utilizes a liquid crystal display circuit of any shape or configuration.

It is still another aspect of the invention is to provide a device, as above, which is portable and which can be worn unobtrusively by the individual.

It is yet another aspect of the invention to provide a device, as above, which can induce a brain wave pattern characterized as the alpha state.

It is yet another aspect of the invention to provide a device, as above, which can induce a variety of brain wave patterns in a subject individual.

It is yet another aspect of the invention to provide a device, as above, which can be fitted to a viewing apparatus, such as spectacles, eyeglass frames, night blinders, caps, head harnesses, etc.

It is yet another aspect of the invention to provide, a device, as above, having a variable timing circuit enabling shadows to be generated at the same or a variety of frequencies.

The achievement of these aspects and others detailed more fully in the following description, are achieved by: A shadow generating apparatus, comprising: a viewing apparatus; at least a lens fitted to said viewing apparatus, each said lens having disposed therein a liquid crystal display; a timing mechanism connected to said liquid crystal; and a power source for said timing mechanism; wherein said timing mechanism intermittently activates and deactivates said liquid crystal.

BRIEF DESCRIPTION OF THE DRAWINGS

In order to gain a fuller insight into the aspects and workings of the invention, a reading of the description of the invention should be accompanied with reference to the following figures, wherein.

BEST MODE FOR CARRYING OUT THE INVENTION

Figure 1:
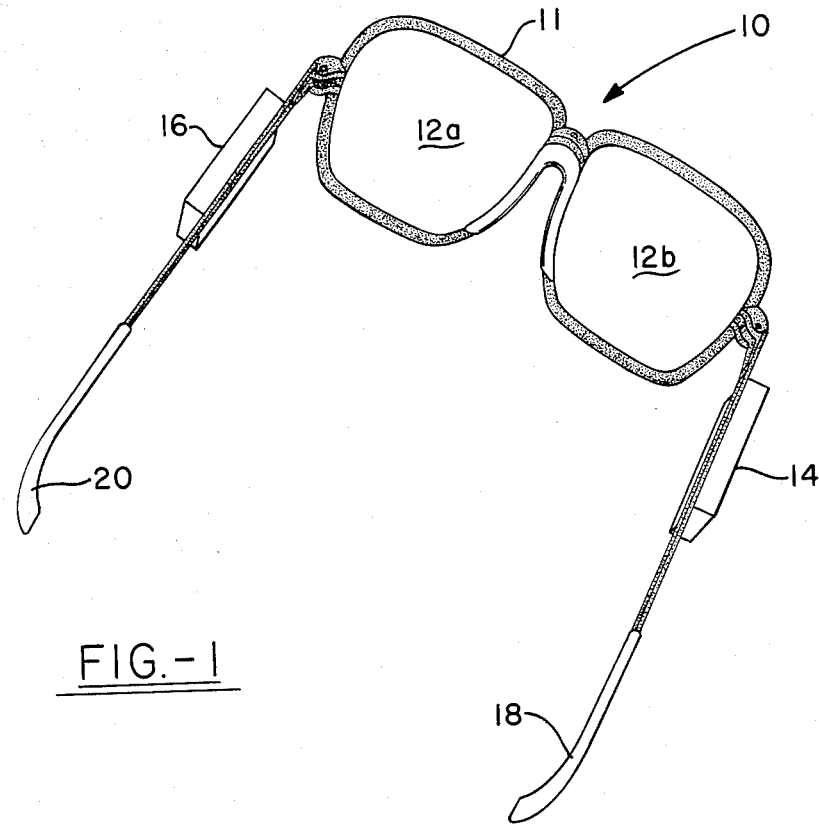
FIG. 1 is a perspective view of the invention utilizes a pair of spectacles.

The salient features of the invention are depicted in FIG. 1, wherein a shadow generating apparatus is designated generally by the number 10. A viewing apparatus in the form of spectacle frames 11 is adapted to receive left and right liquid crystal lenses 12a and 12b, a battery pack 14 and a timing pack 16, both packs positioned on arms 18 and 20 respectively. The shadow generating device 10 is worn by the subject individual in normal fashion so that the lenses 12a and 12b are in the direct line of vision. The liquid crystals in the lenses are then activated periodically by a timing mechanism in the timing pack 16 so that the subject's vision is alternatively blocked and unimpeded.

Figure 3:
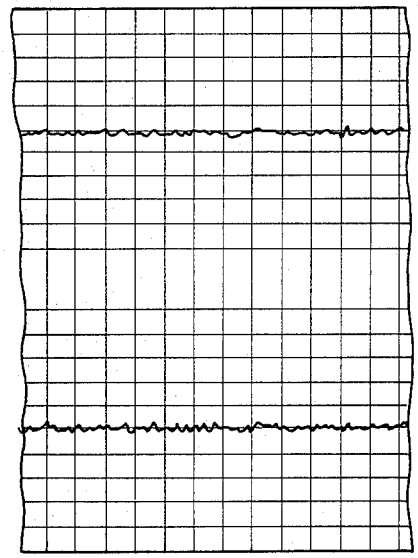
FIG. 3 is a normal beta brain wave chart.
Figure 4:
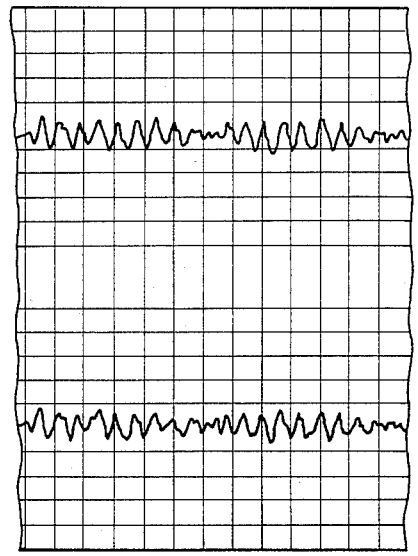
FIG. 4 is a normal alpha brain wave chart.

It has been discovered that, if the correct timing frequency of the LCD lenses is used, the subject's brain will respond accordingly, attempting to match the frequency of shadow generation by a sympathetic brain wave output. Typical human brain wave outputs are illustrated in FIGS. 3 and 4. FIG. 3 is an electroencephalogram of a brain in its normally active or "beta" state. As seen in the Figure, with the graph moving at about 330 millimeters per second, the frequency is above 13 cycles per second.

Lower frequency alpha waves are shown in FIG. 4 which illustrates the brain wave output of a subject utilizing the shadow generating apparatus. When in the alpha state, the brain puts out a frequency of between 8 and 13 cycles per second and the mood of the individual is characterized as relaxed alertness. To obtain such a state, the shadow generating apparatus is set to a frequency between 1 and 6 cycles per second.

If the shadow timing is maintained between 1 and 6 cycles per second, the brain is encouraged to fall into the "theta" state wherein it emits a wave frequency of between 4 and 8 cycles per second and the individual is in a "dreamy" condition. From theta, the individual can easily slip into the "delta" or deep sleep state, having the brain wave frequencies between 0.5 to about 4 cycles per second.

Because the invention has the capability to varying the frequency of shadow generation across a broad range, any of the above described states can be achieved. Of particular interest is the alpha state however, as this represents the level of brain activity most conducive to learning and which can take full advantage of the invention's unique characteristics. The connection between learning and the alpha state has been described in *Superlearning,* Ostrander, et al, Delacarte, New York, New York (1979) which is hereby incorporated by reference. The individual using the invention, at timing frequencies above about 1 cycle per second, becomes quickly accustomed to the intermittent shadows. Thus activities such as listening to tapes, lectures and the like are carried out in a hyper-attentive state. Attaining the alpha state may also be desirable simply for purposes of relaxation rather than learning per se. For this purpose, the subject may close his eyes and allow the shadow generating apparatus to cast perceivable shadows through the closed eyelids. A meditative state may be obtained.

In similar fashion, theta and delta states are initiated by continuing the frequency of shadow generation as outlined above. The subject is most advantageously in a supportive position such as lying down on a couch or bed, or reclining in a chair. With the eyes again closed the invention generates shadows which are perceived through the eyelid to produce the required effect.

Figure 2A:
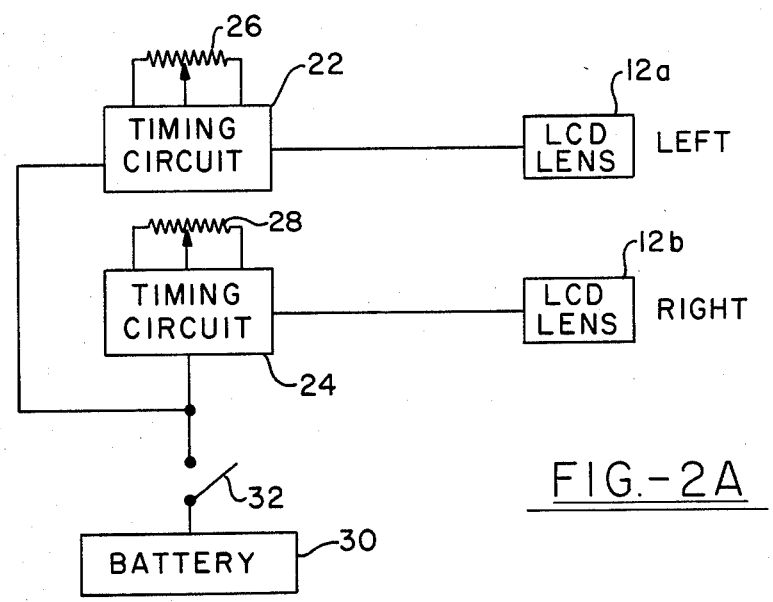
FIG. 2A is a schematic block diagram showing the essential features of the invention's electrical circuit and FIG. 2B is a more detailed schematic of such circuitry.

Referring now to FIG. 2A, a schematic block diagram of the electrical circuitry of the invention can be seen. As illustrated, the left lens 12a is made transparent or opaque by control of the timing circuit 22. In similar fashion, the right lens 12b is controlled by the timing circuit 24. It will be understood that circuits 22,24 are contained within the timing pack 16 on the left arm or temple piece 20. The frequency of repetitive energization of the LCD lens 12a is adjustable by means of a potentiometer 26. In similar fashion, the right lens 12b is regulated by the potentiometer 28. Of course, a switch 32 is provided for activation of the circuitry. The switch 32 may readily be provided in conjunction with the battery pack 14 which contains a battery 30, while appropriate adjustment means such as turn knobs or levers, associated with the potentiometers 26,28 may be provided in association with the timing pack 16. Such elements provide the user with the means for energizing the circuit and regulating the frequency of activation of the lenses.

Figure 2B:
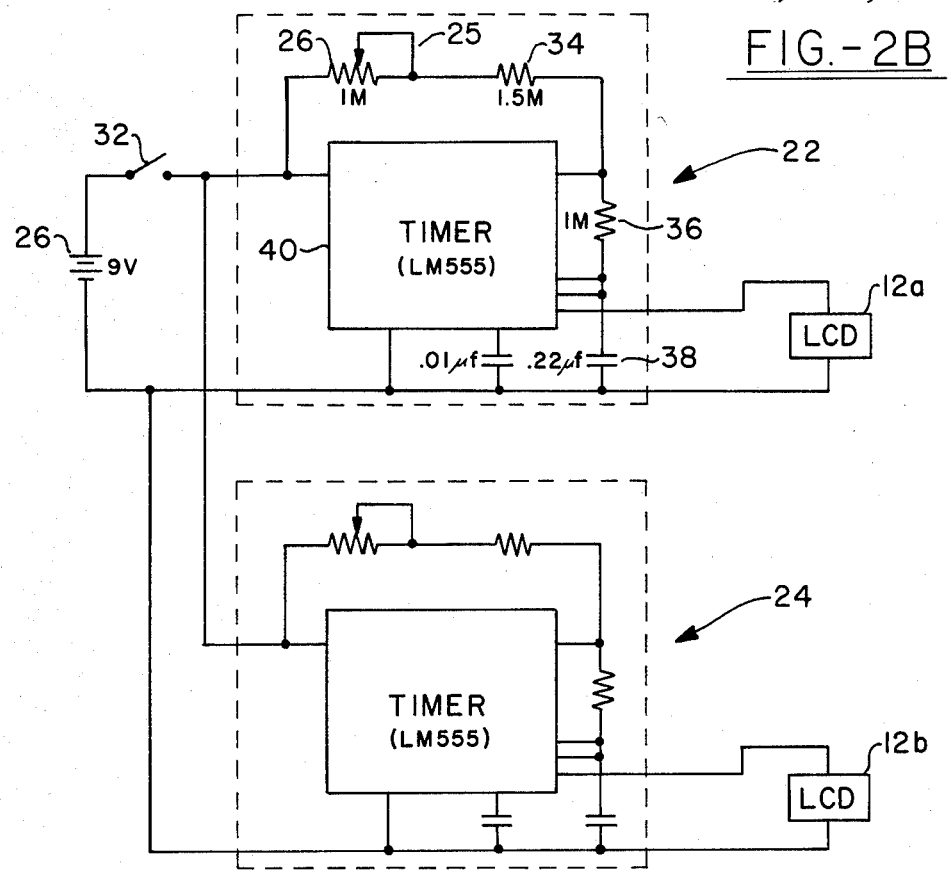

A more detailed schematic of the circuitry of FIG. 2A is presented in FIG. 2B. Here it is illustrated that the basic timing function of the circuits 22,24 is provided by means of a timer such as Model LM555, as sold by National Semiconductor, Texas Instruments, Motorola, or any of numerous semiconductor manufacturers. Suffice it to say that any of numerous off-the-shelf timing circuits would be available to satisfy the needs of the invention herein. In any event, as illustrated for the left timing circuit 22, the potentiometer 25 is adjusted to regulate an RC network comprising potentiometer 26, resistors 34,36, and capacitor 38. The regulation of this potentiometer varies the output signal to the LCD of the left lens 12a. This control changes the output frequency of the timer 40 and, in so doing, adjusts the duty cycle of the same. The output of the timer 40 passes through the LCD left lens 12a and is returned to the negative side of the battery 26 as shown. It will be readily understood by those skilled in the art that the circuitry of the right timing circuit 24 is substantially identical to that of the circuit 22.

With the circuitry just described, the operator may actuate the shadow generating apparatus 10 by closing the switch 32. He may then adjust the frequency of opening and closing of the lenses 12a, 12b by appropriate adjustment of the potentiometers 26,28. Of course, it will be appreciated that this adjustment can be made to cause the lenses 12a, 12b to operate either synchronously or asynchronously. If desired, a single RC circuit could be used to control the output frequency of both the left and right timing circuits 22,24 to assure synchronous operation.

Because each liquid crystal lens has a separate timing mechanism each eye can receive different stimulus which in turn affects the opposite brain hemisphere. As is well known, each hemisphere of the brain performs optimally in different areas. Through frequency variation, it may be possible to "fine-tune" each brain hemisphere as to brain wave output.

As mentioned previously, one of the advantages of the invention is the unobtrusiveness of the shadow generating apparatus. While not shown in the drawings, it will be appreciated that miniaturization of the timing mechanism and the battery pack enables both to be hidden in the arms of the spectacles in a fashion similar to that used for hearing aids. Alternatively, the battery and circuitry can be located in the rim surrounding the lenses or indeed may be located remotely on the subject's body, such as on the head and connected to the spectacles by appropriate wiring. Further, the liquid crystals may not comprise the whole lens area, but rather need only be large enough to be perceived by the individual wearing the spectacles. The liquid crystal may be positioned off center or even at the peripheral edge of the user's vision and still remain effective. Liquid crystals displays as small as 1 millimeter by 1 millimeter have been used successfully, but those of from about 1 inch to a size filling the spectacle rim, i.e., about 4 inches by 4 inches, are preferred. LCD's as large as 10 inches by 10 inches could be used.

While the spectacle frames in the drawing are of conventional design, the invetnion is not linked to such. For example, rather than comprising separate lenses 12a and 12b, a single frame may accomodate but one lens with an LCD positioned therein in such a way that it is perceived by both eyes simultaneously. Naturally, this embodiment would have only one timing mechanism. Further, suspension of the LCD within the individual's line of sight need not be accomplished by means of spectacles of any sort. Other suitable devices will readily occur to those skilled in the art, such as a cap or harness worn on the head and having suspension means attached at the front thereof. Night blinders may also be adapted to receive one or more LCD's. Suffice it to say that the particular embodiment of the viewing apparatus is an obvious modification and the invention is not limited by any one or more designs.

The time it takes to reach the desired state of mind is of course dependent upon the individual and his state of mind prior to use of the invention. For example, if the subject is already in the alpha state, the time to reach the theta or delta states is considerably shorter than if the subject was initially in the beta state.

While the best mode and the preferred embodiment have been disclosed as required by the Patent Statutes, it should be understood that the invention is not limited thereto or thereby. Modifications in addition to those mentioned above can be made to the invention without departing from the scope thereof. For example, it will be understood that prescription spectacles can be modified so as to incorporate the various parts of the invention disclosed above. Further, the invention need not be powered by a battery pack, but may instead utilize line power from a stationary source. Thus to appreciate the true scope of the invention, reference should be made to the attached claims.

What is claimed is:

1. A shadow generating apparatus, comprising:
   a viewing apparatus;
   at least a lens fitted to said viewing apparatus, each said lens having disposed therein a liquid crystal display;
   a timing mechanism connected to said liquid crystal; and
   a power source for said timing mechanism; wherein said timing mechanism intermittently activates and deactivates said liquid crystal.

2. A shadow generating apparatus according to claim 1, wherein said timing mechanism is adjustable, causing said liquid crystal to open and close at frequencies between 1 and 6 cycles per second.

3. A shadow generating apparatus according to claim 2, wherein said timing mechanism in each said crystal is adjustable.

4. A shadow generating apparatus according to claim 3, where timing mechanism is positioned on said viewing apparatus within a timing pack.

5. A shadow generating apparatus according to claim 4, wherein said shadow generating apparatus has two lenses each having a liquid crystal display and timing mechanism and wherein said displays can be operated asynchronously.

6. A shadow generating apparatus according to claim 5, wherein each said liquid crystal occupies from about 1 inch by 1 inch to about 4 inches by 4 inches of said lens.

7. A shadow generating apparatus according to claim 6, wherein said apparatus is worn by a human subject and said timing mechanisms are adjusted to activate said liquid crystals at a frequency of between 1 and 6 cycles per second, thereby inducing the brain of said subject to emit alpha waves.

8. A shadow generating apparatus according to claim 4, wherein said apparatus is used to induce delta and theta waves in a human subject.

* * * * *